(12) United States Patent
Kim et al.

(10) Patent No.: US 7,078,045 B2
(45) Date of Patent: Jul. 18, 2006

(54) PHARMACEUTICAL COMPOSITION FOR TREATMENT AND PREVENTION OF LIVER FIBROSIS AND CIRRHOSIS

(75) Inventors: Sang-Geon Kim, Seoul (KR); Keon-Wook Kang, Seoul (KR)

(73) Assignee: Sang-Geon Kim (KR)

( * ) Notice: Subject to any disclaimer, the term of this patent is extended or adjusted under 35 U.S.C. 154(b) by 262 days.

(21) Appl. No.: 10/220,667

(22) PCT Filed: Mar. 2, 2001

(86) PCT No.: PCT/KR01/00320

§ 371 (c)(1),
(2), (4) Date: Aug. 30, 2002

(87) PCT Pub. No.: WO01/64215

PCT Pub. Date: Sep. 7, 2001

(65) Prior Publication Data

US 2003/0161877 A1    Aug. 28, 2003

(30) Foreign Application Priority Data

Mar. 2, 2000    (KR) ............................... 2000-10540

(51) Int. Cl.
*A61K 9/00*    (2006.01)
(52) U.S. Cl. ..................... 424/400; 422/439; 422/451; 422/464; 422/489; 514/838
(58) Field of Classification Search ................ 424/400, 424/439, 451, 464, 489; 514/210.19, 810, 514/838

See application file for complete search history.

(56) References Cited

U.S. PATENT DOCUMENTS

| | | | |
|---|---|---|---|
| 3,850,991 A | 11/1974 | Chabardes et al. | |
| 4,105,855 A | 8/1978 | Schulz et al. | |
| 4,248,892 A | 2/1981 | Kanamaru et al. | |
| 4,883,887 A | 11/1989 | Bernhard et al. | |
| 5,449,678 A | 9/1995 | Pines et al. | |
| 5,658,913 A | 8/1997 | Kim et al. | |
| 5,686,436 A | 11/1997 | Van Dyke | |
| 5,786,344 A | 7/1998 | Ratain et al. | |
| 5,942,511 A | 8/1999 | Kwon et al. | |
| 5,993,845 A | 11/1999 | Geerts et al. | |
| 6,046,199 A | 4/2000 | Pamukcu et al. | |
| 6,242,478 B1 * | 6/2001 | Welker et al. | 514/439 |
| 6,294,350 B1 | 9/2001 | Peterson | |
| 6,517,824 B1 | 2/2003 | Kohn et al. | |
| 2004/0053989 A1 | 3/2004 | Prendergast et al. | |

FOREIGN PATENT DOCUMENTS

| | | | |
|---|---|---|---|
| JP | 02268116 | * | 11/1990 |
| WO | WO 96/01127 | | 1/1996 |
| WO | WO 01/76604 | | 10/2001 |

OTHER PUBLICATIONS

Fu T et al, Protective effects of biphenyl dimethyl dicarboxylate on damage in isolated rat hepatocytes by carbon tetrachloride and galactosamine, Apr. 1990, 70(4): 201-4.*
Liu et al, Protection of Oltipraz against the hepatotoxicity of Aflatoxin B in the rat, Toxicology and Applied Pharmacology, vol. 93, 442-451 (1988).*
Kensler et al, J Cell Biochem Suppl, 1995; 22:101-7.*
International Search Report for International Application No. PCT/KR01/00319 dated Jun. 21, 2001.
M.H. Davies, et al., "Oltipraz-Induced Amelioration and Acetaminophen Hepatotoxicity in Hamsters", Toxicology and Applied Pharmacology 109, 29-40 (1991).
T.W. Kensler et al., "Mechanism of Protection against Aflatoxin Tumorigenicity in Rats Fed Oltipraz and Related 1,2-Dithiol-3-thiones and 1,2-Dithiol-3-ones", Cancer Research 47, 4271-4277, Aug. 15, 1987.
A.M. Di Bisceglie et al., "Hepatocellular Carcinoma", Hepatology vol. 28, No. 4, 1998, pp. 1161-1165.
P.J. O'Dwyer et al., "Modulation of Gene Expression in Subjects at Risk for Colorectal Cancer by the Chemopreventive Dithiolethione Oltipraz", J. Clin. Invest., The American Society for Clinical Investigation, Inc., vol. 98, No. 5, pp. 1210-1217, Sep. 1996.

(Continued)

*Primary Examiner*—Screenivasan Padmanabhan
*Assistant Examiner*—Sharmila Gollamudi
(74) *Attorney, Agent, or Firm*—Cantor Colburn LLP

(57) ABSTRACT

A pharmaceutical composition for treatment and prevention of liver fibrosis and cirrhosis, which comprises 5-(2-pyrazinyl)-4-methyl-1,2-dithiol-3-thione (oltipraz) and dimethyl-4,4'-dimethoxy-5,6,5',6'-dimethylene dioxybiphenyl-2,2'-dicarboxylate (DDB) as major components, is provided. The ratio of oltipraz and DDB of said composition is preferably 25:0–25, more preferably 5:0.1–5, particularly preferably 5:1. Oltipraz/DDB formulations according to the present invention exhibit surprisingly good effect on the treatment and prevention of liver fibrosis and cirrhosis and are safe drugs that have low toxicity in the human body.

14 Claims, 11 Drawing Sheets

OTHER PUBLICATIONS

S.G. Kim et al., "Enhancement of Radiation-Inducible Hepatic Glutathione-S-Transferases Ya, Yb1, Yb2, Yc1, and Yc2 Gene Expression by Oltipraz: Possible Role in Radioprotection", Molecular Pharmacology, 51, pp. 225-233 (1997), The American Society for Pharmacology and Experimental Theraputics.

P. Pepin et al., "Effects of sulindac and oltipraz on the tumorigenicity of 4-(methylnitrosamino)1-(3-pyridyl)-1-butanone in A/J mouse lung", Carinogenesis, vol. 13, No. 3, pp. 341-348, (1992).

R.W. Ruddon, M.D., Ph.D., Cancer Biology, Third Edition, Oxford University Press, 1995, pp. 61-95, 496-509.

S.S. Ansher et al., "Chemoprotective Effects of Two Dithiolthiones and of Butylhydroxyanisole Against Carbon Tetrachloride and Acetaminophen Toxicity", Hepatology, vol. 3, No. 6, pp. 932-935, 1983.

W.J. Chi et al., "Oltipraz, a novel inhibitor of hepatitis B virus transcription through elevation of p53 protein", Carcinogenesis vol. 19 No. 12, pp. 2133-2138, 1998.

E. Grupta et al., "Pharmacokinetics and Pharmacodynamics of Oltipraz as a Chemopreventive Agent", Clinical Cancer Research vol. 1, pp. 1133-1138, Oct. 1995.

M.L. Clapper et al., "Coordinate Induction of Glutathione S-Transferase $\alpha$, $\mu$, and $\pi$Expression in Murine Liver after a Single Administration of Oltipraz", Molecular Pharmacology, 45:469-474.

N.E. Davidson et al., "Transcriptional Control of Glutathione S-Transferase Gene Expression by the Chemoprotective Agent Oltipraz in Rat Liver", Cancer Research 50, pp. 2251-2255, Apr. 15, 1990.

S.J. Chavan, et al., "Inactivation of Human Immunodeficiency Virus Type 1 Reverse Transcriptase by Oltipraz: Evidence for the Formation of a Stable Adduct", Archives of Biochemistry and Biophysics vol. 324, No. 1, Dec. 1, pp. 143-152, 1995.

H.J. Prochaska et al., "Inhibition of Human Immunodeficiency Virus Type 1 Replication by 7-Methyl-6,8-bis(methylthio)pyrrolo[1,2-$\alpha$]pyrazine, an *In Vivo* Metabolite of Oltipraz", Molecular Pharmacology, 48:15-20 (1995).

Y.Y. Maxuitenko et al., "Identification of dithiolethiones with better chemopreventive properties than oltipraz", Carcinogenesis vol. 19 No. 9 pp. 1609-1615, 1998.

J. Seong et al., "Early alteration in TGF-beta mRNA expression in irradiated rat liver", Pub/Med, National Library of Medicine, one page.

Surh et al., Inhibition of covalent DNA binding and . . . , Mutation research, 1996, vol. 367, pp. 219-224.

Bu et al., Stability, blood partition and protein binding of . . . , Res Commun. Mol. Pathol. Pharmacol., (abstract only), 2001, vol. 109(5-6), pp. 333-344.

Kim, et al., Molecular Basis for hepatic detoxifying . . . , Drug metabolism and disposition, Jun. 1999, vol. 27(6), pp. 667-673.

Bruix et al., Hepatitis B virus and Hepatocellular carcinoma., EASL International Concensus Conference on Hepatitis B(Reproduced from Hepatol.), 2001, vol. 35, p. 421-430.

Mary G. Bolton et al.; "Transient Intervention with Oltipraz Protects against Aflatoxin-induced Hepatic Tumorigenesis"; Cancer Research 53, 3499-3504, Aug. 1, 1993.

James A. Crowell et al.; "Chronic Toxicity Studies of 5-(2-Pyrazinyl)-4-methyl-1,2-dithiole-3-thione, a Potential Chemopreventive Agent", Fundemental and Applied Toxicology 35 (1997), Article No. FA962256, pp. 9-21.

Kenji Kawamura, M.D., et al., "Intranuclear Localization of Proliferating Cell Nuclear Antigen During the Cell Cycle in Renal Cell Carcinoma", $2^{nd}$ Quantitative Cytology and Histology; vol. 22, No. 2/Apr. 2000; p. 107-113.

Linda E. Greenbaum et al.; "CCAAT Enhancer-binding Protein $\beta$is Required for Normal Hepatocyte Proliferation in Mice after Partial Hepatectomy"; The American Society for Clinical Investigations, Inc., vol. 102, No. 5, Sep. 1998, pp. 996-1007.

Davies, M.H. et al: Oltipraz-Induced Changes in Acetaminophen Disposition in Male Hamsters; The Toxicologist, $25^{th}$ Anniversary Meeting, vol. 6, No. 1, Mar. 1986.

Supplementary Partial European Search Report Dated Jun. 9, 2004.

Kang Keon Wook, et al: "The anti-fibrogenic effect of a pharmaceutical composition of '5-(2-pyrazinyl)-4-methyl-1,2-dithiol-3-thione! (oltipraz) and dimethyl-4,-4'-dimethoxy-5,6,5',6'-dimethylene dioxybiphenyl-2,2'-dicarboxylate (DDB)." Archives of Pharmacal Research, Oct. 2002, vol. 25, No. 5, Oct. 2002, pp. 655-663, XP009031942.

Williams et al., "Human aflatoxicosis in developing countries: a review of toxicology, exposure, potential health consequences, and interventions", Am J Clin Nutr (2004) 80: 1160-22.

* cited by examiner

PHARMACEUTICAL COMPOSITION FOR TREATMENT AND PREVENTION OF LIVER FIBROSIS AND CIRRHOSIS

BACKGROUND OF INVENTION

1. Field of Invention

The present invention relates to a pharmaceutical composition for the treatment and prevention of liver fibrosis and cirrhosis. Specifically, the present invention relates to a pharmaceutical composition for the treatment and prevention of liver fibrosis and cirrhosis, comprising 5-(2-pyrazinyl)-4-methyl-1,2-dithiol-3-thione (oltipraz) and dimethyl-4,4'-dimethoxy-5,6,5',6'-dimethylene dioxybiphenyl-2,2'-dicarboxylate (DDB) as major active ingredients.

2. Description of Related Art

Liver plays a key role in the metabolism of xenobiotics and metabolism of endogenous substances and is an important organ with consistent enzymatic reactions and energy metabolism. Among many chronic diseases in Korea, hepatitis, cirrhosis, and liver cancer are the most widespread and life threatening diseases next to cardiovascular diseases. As Korea has a relatively large population of drinkers when compared to developed countries, and as the liver injuries resulting from binge drinking are fairly high, a lot of attention has been paid to treat liver diseases. Often chronic liver damage resulting from viral infection or alcohol drinking causes cirrhosis or liver cancer. In consideration of the physiological characteristics and significance of liver tissues, and in light of the importance of treating and preventing liver diseases, demand is high for the ultimate development of therapeutic and preventive drugs against liver damage.

Various substances, including several synthetic compounds and galenical preparations, show hepatoprotective functions both in vitro and in vivo. Although it has been known that silymarin or betaine have liver protective effects with the action mechanism of cytokine inhibition and increase in the level of glutathione, a curative effect would be hard to expect because of its low effectiveness. As no appropriate curative agents against liver diseases are currently available, the said agents are frequently used for clinical trials. Malotilate and its derivatives, the indication of which is the treatment of liver fibrosis, protect the liver from toxic chemicals and the possible mechanism of action include the induction of phase II conjugating enzymes and the inhibition of cytochrome P450s. However, the compounds non-selectively inhibit several cytochrome P450s and show only preventive effect.

It is known that several substituents of sulfur containing dithiolthione which naturally occurs in cruciferous vegetables, have liver protecting effects. Among them, oltipraz was used as a curative agent against schistosomiasis with the following formula.

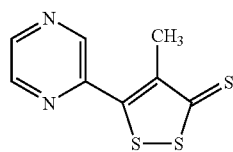

Oltipraz increases cellular thiol content and induces the expression of enzymes responsible for maintaining the glutathione (GSH) pool and detoxifying the tissue from electrophilic molecules. The activities of the following enzymes are increased by oltipraz: NAD(P)H quinone reductase, microsomal epoxide hydrolase, glutathione S-transferase (GST) and UDP-GT. In particular, GST protects the liver from some toxic chemicals such as carbon tetrachloride or acetaminophen (Ansher S S, Dolan P, and Bueding E. Chemoprotective effects of two dithiolthiones and of butyl-hydroxyanisole against carbon tetrachloride and acetaminophen toxicity. 1983 Hepatology 3,932–935).

Furthermore, oltipraz inhibits chemical carcinogenesis caused by benzo[a]pyrene, NDEA, and uracil mustard as well as aflatoxin B1-induced hepatic tumorigenesis and azoxymethane-induced colon carcinogenesis (Bolton M G, Munoz A, Jacobson L P, Groopman J D, Maxuitenko Y Y, Roebuck B D, and Kensler T W. Transient intervention with oltipraz protects against aflatoxin-induced hepatic tumorigenesis. 1993, Cancer Res. 53, 3499–3504).

The known inhibitory mechanisms of carcinogenesis by oltipraz are the followings. First, oltipraz increases the level of an antioxidant, reduced GSH, in tissues. Second, it inhibits bioactivation of carcinogens by inhibiting phase I enzymes such as cytochrome P450. Third, it promotes detoxification of carcinogens by inducing phase II detoxifying enzymes including GST and UDP-GT. Fourth, oltipraz inhibits replication of the human immunodeficiency virus (HIV) type I in vitro. Fifth, it removes reactive intermediates in cells by increasing thiol levels and promotes DNA repair. It has been reported that oltipraz increases GSH levels in most tissues and removes free radicals generated by radiation or xenobiotics. It also has been known that oltipraz functions as a protective agent against radiation by helping to maintain cellular homeostasis.

In regards to the above description, more detailed information will be set out below. Cancer is uncontrolled cell growth and differentiation presumably caused by DNA damages in somatic cells (Cancer Biology, 3rd ed. Raymond W. Ruddon, pp. 61–95, 497–507, Oxford Press). Anticancer effects of chemical agents primarily rely on their antimutagenesis effects or their activity in suppressing transformation into cancer cell or proliferation of cancer cells. Oltipraz has been studied as a cancer chemopreventive agent (Ansher et al., 1983; Bolton et al., 1993). Cancer chemopreventive effects of oltipraz is associated not only with inhibition of cytochrome P450 3A, but also with induction of phase II detoxifying enzymes. Expression of glutathione S-transferase (GST) is increased by oltipraz in cells and animals (Clapper et al., 1994; Davidson et al., 1990), which is associated with suppression in toxicant-induced tissue injuries and carcinogenesis (Kensler et al., 1987; Maxuitenko et al., 1998). Oltipraz protects the liver against tissue damage caused by radiation (Kim et al., 1997), and GST induction known from the prior study means cellular adaptive response. Oltipraz also protects the liver against toxicants (Ansher et al., 1983). Inhibition of aflatoxin B1-induced carcinogenesis by oltipraz is mediated through the intervention of cytochrome P450 3A-catalyzed metabolic activation of carcinogen. According to recent clinical trials, oltipraz was effective in lowering plasma aflatoxin B1 levels of people at high risk of liver cancer. Aflatoxin B1-induced carcinogenesis in animals was also reduced by the application of oltipraz.

It has been reported that oltipraz inhibits hepatitis B virus (HBV) replication in 2.2.15 cells, which were infected with HBV DNA-containing plasmid. Therefore, oltipraz inhibits transcription of hepatitis B virus gene, elevates p53 protein expression (Chi et al., 1998), and inhibits human immunodeficiency virus (HIV) replication (Prochaska et al., 1995).

Cinical trials in regard to the chemopreventive effect of oltipraz against liver carcinogenesis has been conducted in China. The results showed that oltipraz had weak protective effects against liver carcinogenesis. It is also known that oltipraz protects the liver against toxicant-induced hepatotoxicity, at least moderately. In addition, the safety of oltipraz has been proven in toxicity studies performed in rats and dogs (Fund. Appl. Toxicol. 1997 January; 35(1):9–21).

DDB (dimethyl-4,4'-dimethoxy-5,6,5',6'-dimethylene dioxybiphenyl-2,2'-dicarboxylate), a component derived from Shizandrae, is a curative agent for the treatment of hepatitis clinically used in East Asia, including Korea. DDB protects the liver tissue against carbon tetrachloride-, galactosamine-, thioacetamide- or prednisolone-induced injuries and enhances antibody production. Having been known to be effective in clinical trial for the patients with hepatitis, DDB is used widely in the clinical setting. The present inventors reported that DDB's pharmacological effect was associated with the inhibition of NF-κB activation and TNF-β production. Further, it was found that DDB did not affect the expression of drug metabolizing enzymes. Since NF-κB is known as a transcription factor mediating the inflammatory response, an inhibitor of NF-κB would be capable of inhibiting systemic inflammatory response.

Liver fibrosis means a prepathological state wherein damaged liver tissues in chronic liver diseases such as hepatitis are not repaired into normal tissues, but are converted to fibrous tissues such as collagen as part of an in vivo adaptive response.

Although liver fibrosis is outcome of an in vivo repair process in response to tissue damage, damaged liver tissues are replaced by fibrous tissues, which can no longer function normally (e.g. in vivo metabolism or bile juice production). As continuous and recurring liver fibrogenesis leads to cirrhosis and eventually causes death, it is crucial to develop new drugs to treat liver fibrosis. However, as the precise mechanism of liver fibrogenesis is not known, appropriate curative drugs have not yet been developed.

Recent studies revealed that transforming growth factor-beta (TGF-β), a cytokine secreted from Kupffer and Ito cells in the liver, was an important mediator in liver fibrosis. In addition, it was reported that blocking TGF-β activity by employing TGF-β antibodies, antisense RNA, and modifications to TGF-β receptors significantly decreases liver fibrosis. However, the effects of said research have only been confirmed at the experimental level. Clinical viable drugs for liver fibrosis and cirrhosis have not been reported.

OBJECT OF THE INVENTION

The present invention provides a pharmaceutical composition that maximizes the treatment effectiveness of hepatic fibrosis and cirrhosis, and that can be used as a preventive agent as well.

Further, the present invention provides a use of a pharmaceutical composition used in the preparation of medicine for the treatment and prevention of hepatic fibrosis and cirrhosis.

Still, the present invention provides a method of treating or preventing hepatic fibrosis and cirrhosis, which comprises administering a pharmaceutical composition to a mammal.

SUMMARY OF THE INVENTION

The present invention provides a pharmaceutical composition for treatment and prevention of liver fibrosis and cirrhosis, which comprises 5-(2-pyrazinyl)-4-methyl-1,2-dithiol-3-thione (oltipraz) and dimethyl-4,4'-dimethoxy-5,6,5',6'-dimethylene dioxybiphenyl-2,2'-dicarboxylate (DDB) as major components. The ratio of oltipraz and DDB of said composition is preferably 25:0–25, more preferably 5:0.1–5, and most preferably 5:1. Oltipraz/DDB formulations according to the present invention exhibit surprisingly good effect on the treatment and prevention of liver fibrosis and cirrhosis, and are safe drugs that have low toxicity in the human body.

BRIEF DESCRIPTIONS OF DRAWINGS

DETAILED DESCRIPTION OF INVENTION

Figure 1:
FIG. 1 is a photograph showing the inhibition effect of oltipraz on TGF-β1 mRNA expression in liver tissue when DMN is administered to a rat.

The present inventors have made the unprecedented discovery that the oltipraz has an unexpectedly surprising effect of treating and preventing hepatic fibrosis and cirrhosis. Further, they have discovered that the treatment and prevention effectiveness of oltipraz increases significantly when combined with DDB.

Fibrosis, a preliminary stage of cirrhosis, occurs when severe damage is done to the liver by a variety of factors. Cirrhosis is partially related to carcinogenesis and notably increases the risk of liver cancer in its victims. However, the pathological mechanism of cirrhosis is clearly distinguishable from liver cancer. That is, hepatic fibrosis occurs when there is chronic and severe damage to hepatic tissue. The causative factors for liver damage include viruses, parasites, alcohol consumption, chemicals, and medicines. Hepatic fibrosis occurs through the over-production of the extracellular matrix (e.g., type I, III and IV collagen) caused by the activation of non-parenchymal cells in hepatic tissue, such as Kupffer cells, stellate cells, etc. More specifically, fibrosis occurs from the activation and subsequent transformation of stellate cells into myofibroblasts. The activated stellate cells then produce excess extracellular matrices. Furthermore, fibrosis and cirrhosis are clearly distinguishable as pathological phenomena apart from viral hepatitis and liver cancer. Thus, their respective treatments and preventions are also distinguishable. However, currently, there is no clinically viable drug for hepatic cirrhosis.

The present invention is based on the discovery that oltipraz, known to be effective in the prevention of liver cancer, is also effective against liver fibrosis and cirrhosis, which are completely different in their pathological mechanisms from liver cancer. Further, the present invention features the use of oltipraz with DDB, previously known to be effective only against hepatitis, providing effectiveness beyond expectations in treating and preventing liver fibrosis and cirrhosis. These facts are proven in the experiments described below.

Oltipraz or oltipraz/DDB decreases the fibrosis score and Knodell score, indicators of dimethylnitrosamine (DMN) accelerated fibrosis. This coincides with exemplary tissue microscopy examinations. Additionally, upon administration, oltipraz or oltipraz/DDB significantly inhibits hepatotoxicity indicators such as ALT, AST, bilirubin, and gamma-glutamyl transpeptidase (gamma-GT). This shows that oltipraz or oltipraz/DDB may ameliorate fibrosis by retarding their respective processes. The oltipraz or oltipraz/DDB fibrosis inhibition mechanism revolves around the inhibition of TGF-$\beta$ expression. According to quantitative RT-PCR results, oltipraz or oltipraz/DDB completely inhibits TGF-$\beta$ mRNA expression accelerated by dimethylnitrosamine. This serves as evidence that oltipraz is a drug that is capable of inhibiting the genesis and progression of hepatic fibrosis and cirrhosis. Oltipraz induces the hepatic detoxification enzymes GST and mEH, increases GSH, and exhibits radical conjugating activity; on the contrary, DDB does not induce detoxification enzymes. In view of the above, it is believed that oltipraz and DDB have complementary pharmacological effects. More specifically, as the inhibition of CYP3A metabolic activity by DDB in human liver microsomes is believed to subsequently inhibit the metabolism of oltipraz, even a low dosage of oltipraz may provide potent liver protection and lengthen the effective duration of the drug.

In the present invention, the curative effects of oltipraz/DDB combinations on hepatic fibrosis were observed at various ratios in rats that had been administered with DMN. The test was conducted for the weight ratio of 25:5, 15:15 and 5:25 (mg/kg) of oltipraz:DDB. In the results, when DMN was administered (observation was conducted 1 week after 3 weeks of administration), ALT, AST, bilirubin, gamma-glutamyl transpeptidase ($\gamma$-GT), the fibrosis score and Knodell score were significantly increased compared to those of the control group. In contrast, when oltipraz/DDB was administered, these values were decreased. Oltipraz (25 mg/kg)/DDB (5 mg/kg) showed the highest hepatic fibrosis inhibiting effect. This proves that oltipraz and DDB show synergism in suppressing liver damage and fibrosis, and teaches that the optimal ratio between them is 5:1. Further, oltipraz/DDB combination administration reduced the blood biochemical indices, i.e. the liver fibrosis score and the Knodell score, more than oltipraz (50 mg/kg) alone. Accordingly, it is believed that using oltipraz with DDB can reduce side effects, such as disorders of the gastrointestinal tract, paraesthesia of the hands and feet, etc.; which can result from high oltipraz dosages. DDB inhibits the inflammatory response induced by DMN, while oltipraz prevents TGF-$\beta$ expression, increases the expression of antioxidant enzymes and induces increases in GSH. By this mechanism, oltipraz/DDB maximizes the effect of treating and preventing liver fibrosis. Thus, oltipraz/DDB utilizes complementary effects for liver protection. Further, oltipraz/DDB can be clinically used since it shows almost no side effects.

It is preferable that the pharmaceutical composition of the present invention be used by combining independently formulated drugs, or by preparing a combination formulation consisting of a mixture of drugs. When the pharmaceutical composition of the present invention is to be used in actuality, unit dosage forms suitable for oral administration are to be formulated and administered according to the conventions of the proper pharmaceutical field. To achieve this, the oral formulation comprises a hard or soft capsule, tablet, powder, etc. The oral formulation, in addition to oltipraz/DDB as the pharmacologically active agent, may contain one or more pharmacologically non-active conventional carrier mediums. For example the oral formulation may contain as additives starch, lactose, carboxymethylcellulose, kaolin, and the like excipients; water, gelatin, alcohol, glucose, arabic gum, tragacanth gum and the like binders; starch, dextrine, sodium alginate, and the like disintegrants; talc, stearic acid, magnesium stearate, liquid paraffin, and the like lubricants. Dissolving aids may be further added.

The daily dosage of the present invention depends on various factors such as the patient's degree of liver damage, time of onset of hepatitis, age, health, complications, etc. However, for the average adult, the oltipraz/DDB composition is administered once or twice a day for a total daily dosage of 5 to 200 mg, more preferably 25 to 50 mg. However, in patients with severe liver damage or when used as an anti-recurring agent after hepatic carcinectomy, the present invention can depart from the scope of the above pharmaceutical composition and employ even large dosages. Most preferably, one or two unit dosages containing 25 mg of oltipraz and 5 mg of DDB are orally administered twice a day.

The pharmaceutical composition of the present invention optimally complements oltipraz, which has remarkable fibrosis inhibiting and liver protecting qualities, with DDB, which has an excellent inflammatory response suppressing effect. The above provides inhibition of liver fibrosis and cirrhosis, has low toxicity, and nearly no side effects. Thus, the present invention may be safely used over the long-term for the treatment and prevention of hepatic fibrosis and cirrhosis.

The present invention will be explained in more detail by the test and working examples below. However, the present invention is not limited to these working examples.

EXAMPLES

TEST EXAMPLES

Test Example 1

Anti-fibrotic Effect of Oltipraz (1)

Rats constantly administered with dimethylnitrosamine (DMN) over a period of 4 weeks displayed a four-fold increase in plasma alanine aminotransferase and aspartate aminotransferase. Upon pretreatment of 50 mg/kg oltipraz, blood plasma ALT and AST activation increases were 50% inhibited (Table 1).

Plasma gamma-glutamyl transpeptidase (gamma-GT) activity and bilirubin content are used as indicators of hepatic functionality. Oltipraz inhibited increases in gamma-GT activation by 70%–80% in DMN administered rats. On the other hand, when DMN was administered, bilirubin content increased eight-fold compared to the control group. When 50 mg/kg oltipraz and DMN were simultaneously administered plasma bilirubin increase was 65% inhibited.

TABLE 1

ALT, AST, gamma-GT, Bilirubin Values

| Group | ALT | AST | gamma-GT | Bilirubin |
|---|---|---|---|---|
| Control | 49 ± 2 | 113 ± 6 | 0.2 ± 0.1 | 0.2 ± 0.01 |
| DMN | 190 ± 12* | 412 ± 39 | 12.1 ± 4.1* | 0.9 ± 0.2* |
| DMN + Oltipraz 50 mg/kg | 116 ± 4# | 246 ± 32# | 2.6 ± 0.5# | 0.3 ± 0.03# |

Each value is represented by the average ± standard deviation. The number of animals used ranged from 8 to 16. The significance of each group was indicated by the Newman-Keuls test of multiple analysis. The significance markers are: *=$p<0.05$ compared to control, #=$p<0.05$ compared to DMN treated group.

Test Example 2

Anti-fibrotic Effect of Oltipraz (2)

The tissue pathological effect of oltipraz on DMN induced hepatic fibrosis was observed in an animal test model. Clear fibrosis was observed in rats administered with DMN over a 4-week period, 3 times a week. When oltipraz (orally administered in 5–50 mg/kg doses, 3 times a week, over 4 weeks) and DMN were administered simultaneously, fibrosis in the hepatic tissue was reduced when compared to DMN administration alone. Hepatic tissue necrosis and fibrosis were pathologically determined through the use of hepatic tissue pathology indicators, namely, Van Gieson's staining and Masson's trichrome staining (Table 2).

50 mg/kg oltipraz dose effectively ameliorated DMN induced fibrosis (Table 2). The degree of fibrosis was determined by evaluating the fibrosis and Knodell scores, which show degrees of liver damage and fibrosis. Compared to the DMN-only group, the DMN+oltipraz group showed lower fibrosis and Knodell scores, showing remedy of liver damage and fibrosis.

TABLE 2

Inhibition Effect of Oltipraz on Hepatic Tissue Fibrosis

| Group | Fibrosis Values | Knodell Values |
|---|---|---|
| Control | 0 | 0 |
| DMN | 3.7 ± 0.5 | 16.1 ± 2.9 |
| DMN + Oltipraz 5 mg/kg | 3.1 ± 0.4* | 11.1 ± 1.7* |
| DMN + Oltipraz 15 mg/kg | 2.9 ± 0.8* | 12.1 ± 1.9* |
| DMN + Oltipraz 50 mg/kg | 2.5 ± 0.9** | 8.0 ± 1.6** |

Each value is represented by the average ± standard deviation. The number of animals used was 8 to 16. The significance of each group is determined by the Newman-Keuls test of multiple analysis. *$p<0.05$, **$p<0.01$. Degree of fibrosis 0=Normal, 1=Presence of weak fibrous tissue, 2=Moderate presence of fibrous tissue, 3=Obvious presence of fibrous tissue, 4=Evidence of severe fibrosis. Sum of values from periportal bridging (Greatest=10), intralobular cell loss (Greatest=4), portal inflammation (Greatest=4), and fibrosis (Greatest=4) yields the Knodell score.

Test Example 3

Pharmacological Mechanism of Oltipraz in Anti-fibrosis

TGF-β 1 is a principal cytokine that rises in expression during fibrosis upon tissue damage. Animal TGF-β 1 mRNA expression was observed under RT-PCR analytical methods during DMN-only administration and DMN and oltipraz simultaneous administration. In animals administered with DMN over 4 weeks, irreversible excess fibrogenesis prevented the observation of TGF-β 1 mRNA expression. TGF-β 1 mRNA expression was observed in DMN-only administered animals. 18 hours after DMN administration, oltipraz was administered. TGF-β 1 mRNA expression was then observed 24 hours later. In DMN administered rats, TGF-β 1 mRNA increased notably in liver tissue. DMN induced expression of TGF-β 1 mRNA was completely inhibited by the administration of 100 mg/kg oltipraz. GAPDH mRNA expression did not change upon either DMN-only administration or DMN and oltipraz simultaneous administration. Therefore, it is shown that oltipraz inhibits hepatic fibrosis through the pharmacological mechanism that reduces TGF-β 1 expression (FIG. 1).

Test Example 4

Evaluation of Oltipraz in Inhibiting TGF-β Production

A test was conducted using RAW264.7 macrophage cells to observe whether oltipraz directly inhibited production of TGF-β, which is over-expressed in macrophages, and to evaluate related molecular pharmacological mechanisms. When oltipraz was directly added to RAW264.7 cells, which had increased TGF-β expression, oltipraz was discovered to inhibit TGF-β expression in a dose-dependent manner. These results show that oltipraz may function as an anti-fibrotic agent in hepatic Kupffer cells by inhibiting TGF-β production. Furthermore, the increase in TGF-β expression is inhibited by EGTA or genistein, which is an inhibitor of tyrosine kinase. This result shows that inhibition of TGF-β production by oltipraz may be the result of intracellular calcium regulation and changes in protein kinase activity (Table 3).

TABLE 3

Inhibition of TGF-β Expression by Oltipraz in Macrophages

|  | Control | Oltipraz 30 μM | Oltipraz 100 μM | EGTA 1 mM | Genistein 100 μM |
|---|---|---|---|---|---|
| TGF-β Inhibition Percentage (%) | 0 | 30 | 60 | 80 | 80 |

Test Example 5

Anti-inflammatory Mechanism of DDB (Inhibition of NF-κB Activation)

It is known that NF-κB activation is associated with inflammatory responses. To compare the NF-κB activity in the liver tissue when DDB is administered with that when DDB is not administered, the following test was conducted. SD male rats with weight of about 150 g were used. For one group 7 rats were used. For the control group (vehicle administered) and test group (20 to 100 mg/kg/day of DDB administered), the NF-κB activity in accordance with the treatment of endotoxin (lipopolysaccharide, LPS) was measured by using Electrophoresis Mobility Shift Assay (EMSA).

LPS treatment (1 μg/kg) resulted in an increase in the level of NF-κB nuclear transcription p50 and p65 complex. However, DDB treatment (20–100 mg/kg) 2 h prior to LPS treatment blocked translocation of the NF-κB complex into the nucleus and its activity. These results show that DDB is capable of inhibiting LPS-inducible NF-κB activation in the rat liver.

Stimulation of Raw264.7 cells with 1 μg/kg of LPS caused an increase in DNA binding activity of NF-κB after 30 min to 1 h. DDB at the concentrations of 0.1, 0.3 and 1 mM inhibited NF-κB activity in a concentration-dependent manner. These results were consistent with those obtained in the livers of rats treated with DDB (Table 4).

TABLE 4

Effect of DDB on NF-κB Activation

| Group | LPS 1 μg/kg or 1 μg/ml | LPS + DDB 20 mg/kg | LPS + DDB 50 mg/kg | LPS + DDB 100 mg/kg | LPS + DDB 0.1 mM | LPS + DDB 0.3 mM | LPS + DDB 1.0 mM |
|---|---|---|---|---|---|---|---|
| % inhibition of NF-κB activation | 0 | 42 | 63 | 73 | 33 | 35 | 65 |

Inhibition of I-κBα Degradation

Translocation of NF-κB to the nucleus was preceded by phosphorylation and proteolytic degradation of the I-κBα subunit. This test was conducted in order to ascertain whether the effect of DDB on NF-κB activation is associated with the inhibition of I-κBα degradation. The level of I-κBα protein was reduced 30 min after the treatment of rats with LPS (1 μg/kg). In contrast, treatment with DDB 2 h prior to LPS treatment attenuated the decrease in I-κBα protein by LPS. Also with RAW264.7 cells, DDB inhibited the degradation of I-κBα protein in a concentration-dependent manner at the concentrations of 0.3 to 1 mM. These results show that DDB inhibits I-κBα degradation and the resultant NF-κB activation (Table 5).

TABLE 5

Effect of DDB on I-κBα Degradation

| | LPS 1 μg/kg or 1 μg/ml | LPS + DDB 100 mg/kg | LPS + DDB 0.1 mM | LPS + DDB 0.3 mM | LPS + DDB 1.0 mM |
|---|---|---|---|---|---|
| % inhibition of I-κBα degradation | 0 | 67 | 22 | 34 | 65 |

Test Example 6

Anti-inflammatory Mechanism of DDB (Inhibition of TNF-α Production and mRNA Expression)

TNF-α is the principal mediator of the responses to LPS and is involved in inflammatory processes. It was determined by ELISA whether the amount of TNF-α released into blood decreases when NF-κB activity was inhibited by DDB. A single dose of LPS treatment (1 μg/kg, i.v.) increased the TNF-α level from 35 to 5160 pg per ml of plasma 2 h after administration. DDB treatment at a dose of 20, 50 or 100 mg/kg prevented the elevation of plasma TNF-α level by LPS, resulting in 1350, 1230 or 690 pg per ml of plasma, respectively. With the RAW264.7 cells, DDB decreased the production of TNF-α by LPS. These results show that DDB inhibited TNF-α expression in macrophages and in the liver (Table 6).

TABLE 6

Effect of DDE on TNF-α Production in Plasma

| | LPS 1 μg/kg or μg/ml | LPS + DDB 20 mg/kg | LPS + DDB 50 mg/kg | LPS + DDB 100 mg/kg | LPS + DDB 1.0 mg/kg |
|---|---|---|---|---|---|
| % inhibition of NF-κB activation | 0 | 74 | 76 | 87 | 65 |

Test Example 7

Anti-fibrotic Effect of Oltipraz/DDB Combination (1)

The anti-fibrotic activity of the oltipraz/DDB combination was evaluated by changing the component ratio of the combination. To evaluate the effect of the combination according to the component ratio, the dosage schedule of DMN was partially modified. That is, while DMN was administered to a rat 12 times totally in dosages of 10 μl/kg per administration over a 4-week period, 3 times a week in the test examples 1 and 2, to evaluate the effect of the combination according to the component ratio, an animal model with reduced liver damage was used wherein DMN was administered to a rat 9 times totally in dosages of 10 μl/kg per administration over a 3-week period, 3 times a week, and then not administered in the remaining one week in the test example.

One week after administering DMN over 3 weeks, a fibrosis score of 2.9 and a Knodell score of 11.7 were shown in the animals. Thus, a reduction of liver fibrosis was shown in the animals when compared with DMN-administered animals over a 4-week period having a fibrosis score of 3.7 and a Knodell score of 16.1.

One week after administering DMN over a 3-week period, 3 times a week, ALT and AST activity in plasma of the animals increased about 4-fold when compared to those of the control group.

In the animals in which oltipraz and DDB were administered with a dosage ratio of 25:5, 15:15 and 5:25 mg/kg over a 3-week period (3 times a week) one day after each administration of DMN, increases in the activities of ALT and AST in the plasma of the animals were significantly inhibited when compared to those of the animals to which only DMN was administered. In comparing the efficacies between the component ratios of the combinations, although the animal group to which oltipraz and DDB were administered with a dosage ratio of 15:15 mg/kg also showed a significant inhibition of ALT and AST activities in plasma, the degree of inhibition was smaller than those of the animals wherein oltipraz and DDB were administered with a dosage ratio of 25:5 mg/kg (Table 7).

γ-GT activity and bilirubin content in plasma is used as a representative indicator of hepatic functionality. In rats in which oltipraz and DDB were administered with a dosage ratio of 25:5, 15:15 and 5:25 mg/kg over a 3-week period, DMN-induced bilirubin content increases were inhibited by a statistically significant degree. Similar to the results of the ALT and AST values, bilirubin increases were best inhibited in the animals wherein oltipraz and DDB were administered with the dosage ratio of 25:5 mg/kg among the animal groups to which oltipraz and DDB were administered.

Total protein content and albumin level in blood are indicators of protein synthesis in liver tissue. When hepatic cirrhosis develops, total protein content in blood generally decreases. One week after administering DMN over a 3-week period, the total protein content significantly decreased in treated animals, but the total protein content recovered to normal control group levels in the animal groups to which oltipraz and DDB were administered with a dosage ratio of 25:5 and 15:15 mg/kg (Table 7).

These results suggest that among the component ratios of oltipraz and DDB used in the test example, the animal group to which 25:5 mg/kg of oltipraz and DDB was administered showed the greatest inhibiting effect against hepatic fibrosis induced by DMN. Also, it can be noted that such effect in the oltipraz (25 mg/kg)/DDB (5 mg/kg)-administered animal group is equal or superior to that of the drug which was observed in the animal wherein 50 mg/kg of oltipraz was administered alone in test example 1. In fact, the inhibition percentage of ALT increase by DMN was 40% in the animal group wherein 50 mg/kg of oltipraz was administered alone, while the inhibition percentage of hepatic fibrosis was 43% when 25:5 mg/kg of oltipraz and DDB were administered. In the case of other indicators, similar results were obtained.

TABLE 7

ALT, AST, Bilirubin, Albumin and Total Protein Content Value

| Group | ALT | AST | Total protein content | Albumin | Bilirubin |
|---|---|---|---|---|---|
| Control group | 44 ± 3 | 114 ± 6 | 6.2 ± 0.1 | 5.1 ± 0.1 | 0.25 ± 0.02 |
| DMN | 169 ± 7* | 222 ± 14* | 5.0 ± 0.2* | 4.0 ± 0.2* | 1.1 ± 0.3* |
| DMN + Oltipraz 25/ DDB 5 mg/kg | 98 ± 9# | 156 ± 8# | 5.9 ± 0.2# | 4.8 ± 0.1# | 0.3 ± 0.04# |
| DMN + Oltipraz 15/ DDB 15 mg/kg | 108 ± 10# | 194 ± 19 | 5.7 ± 0.2# | 4.7 ± 0.1# | 0.4 ± 0.08# |
| DMN + Oltipraz 5/ DDB 25 mg/kg | 127 ± 8# | 206 ± 14 | 5.3 ± 0.1# | 4.3 ± 0.1 | 0.4 ± 0.09# |

Each value is represented by the average ± standard deviation. The number of animals used was 8 to 10. The significance of each group is determined by the Newman-Keuls test of multiple analysis. The significance markers are: *=$p<0.05$ compared to control, #=$p<0.05$ compared to DMN treated group.

Test Example 8

Anti-fibrotic Effect of Oltipraz/DDB (2)

Figure 2A:
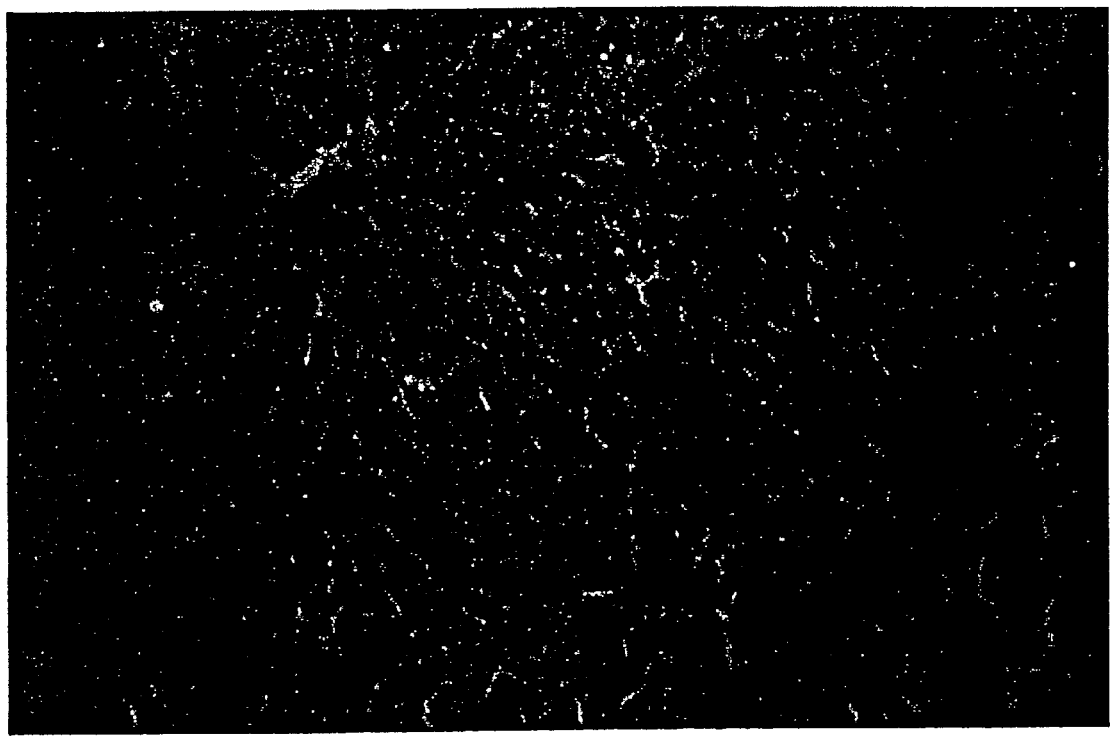
FIG. 2a is a photograph of liver tissue of a normal animal (H&E staining).
Figure 2B:
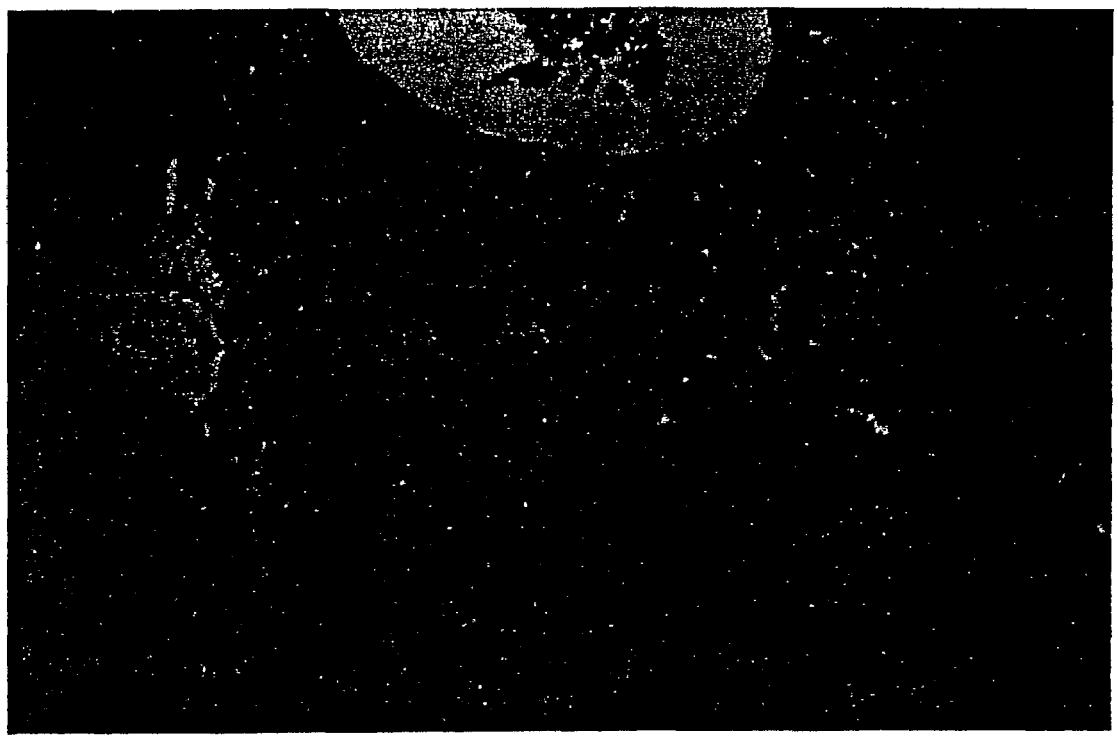
FIG. 2b is a photograph of liver tissue of a normal animal (H&E staining).
Figure 3A:
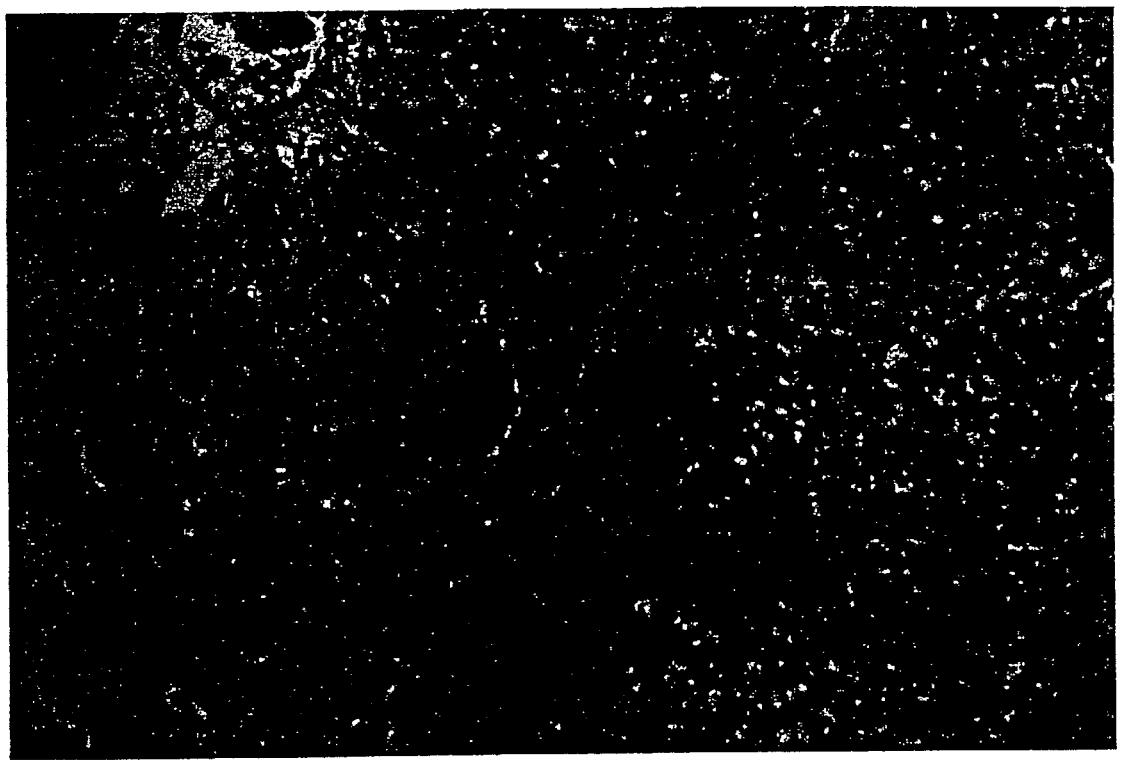
FIG. 3a is a photograph of liver tissue from the group to which DMN was administered (H&E staining).
Figure 3B:
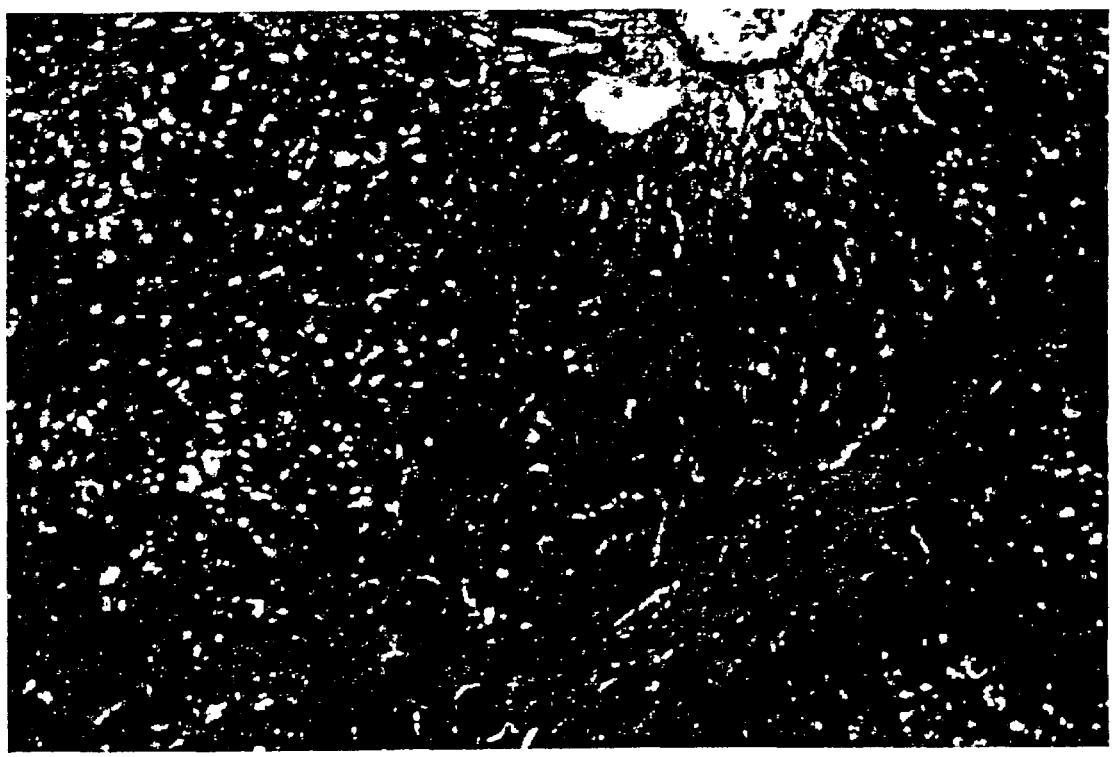
FIG. 3b is a photograph of liver tissue from the group to which DMN was administered (Masson's trichrome staining).
Figure 4A:
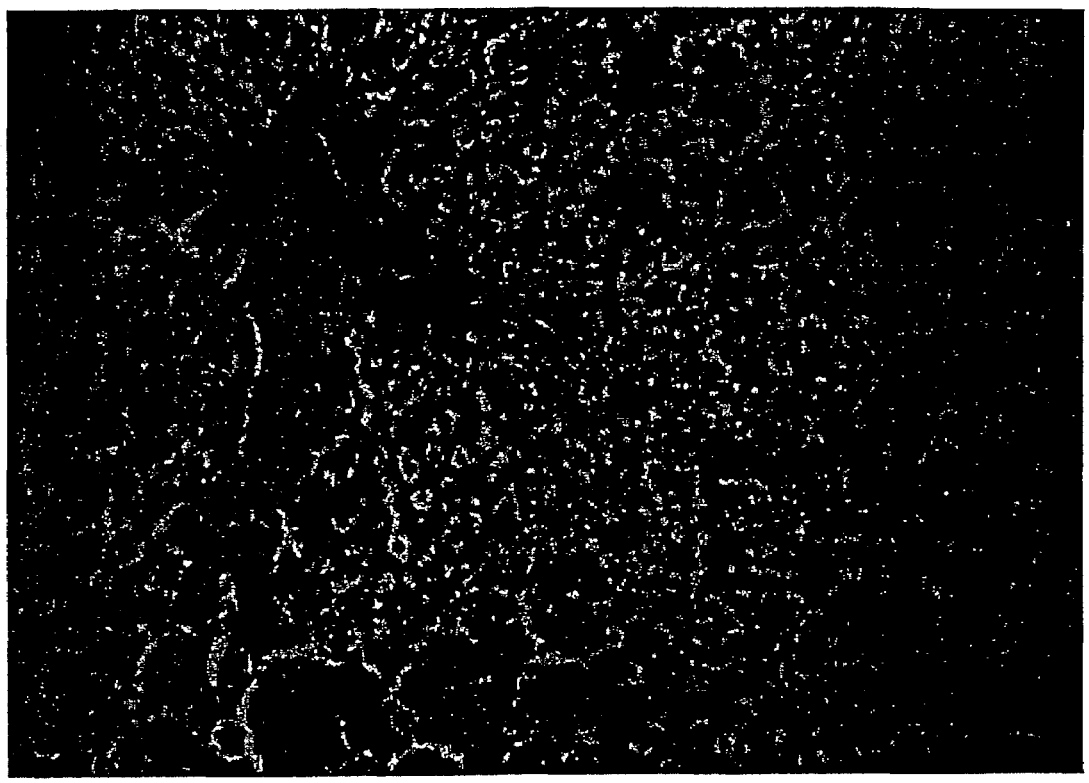
FIG. 4a is a photograph of liver tissue from the group to which DMN and oltipraz (25 mg/kg)/DDB (5 mg/kg) were co-administered (H&E staining).
Figure 4B:
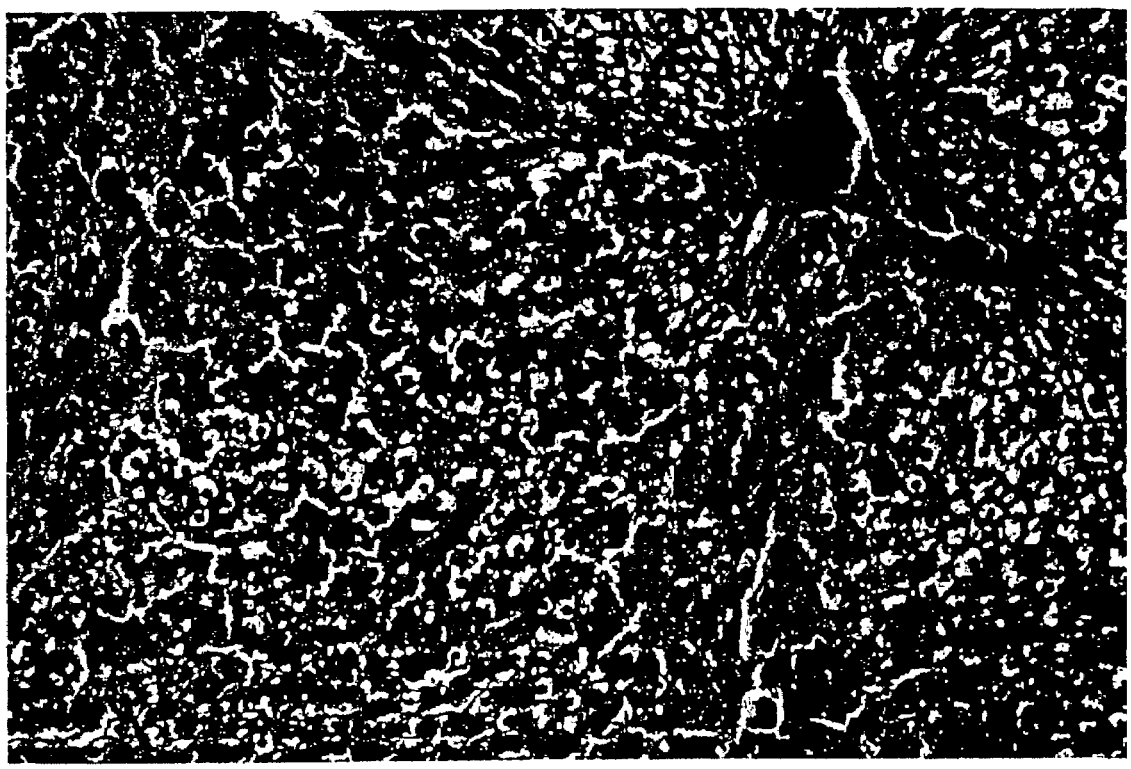
FIG. 4b is a photograph of liver tissue from the group to which DMN and oltipraz (25 mg/kg)/DDB (5 mg/kg) were co-administered (Masson's trichrome staining).
Figure 5A:
FIG. 5a is a photograph of liver tissue from the group to which DMN and oltipraz (15 mg/kg)/DDB (15 mg/kg) were co-administered (H&E staining).
Figure 5B:
FIG. 5b is a photograph of liver tissue from the group to which DMN and oltipraz (15 mg/kg)/DDB (15 mg/kg) were co-administered (Masson's trichrome staining).
Figure 6A:
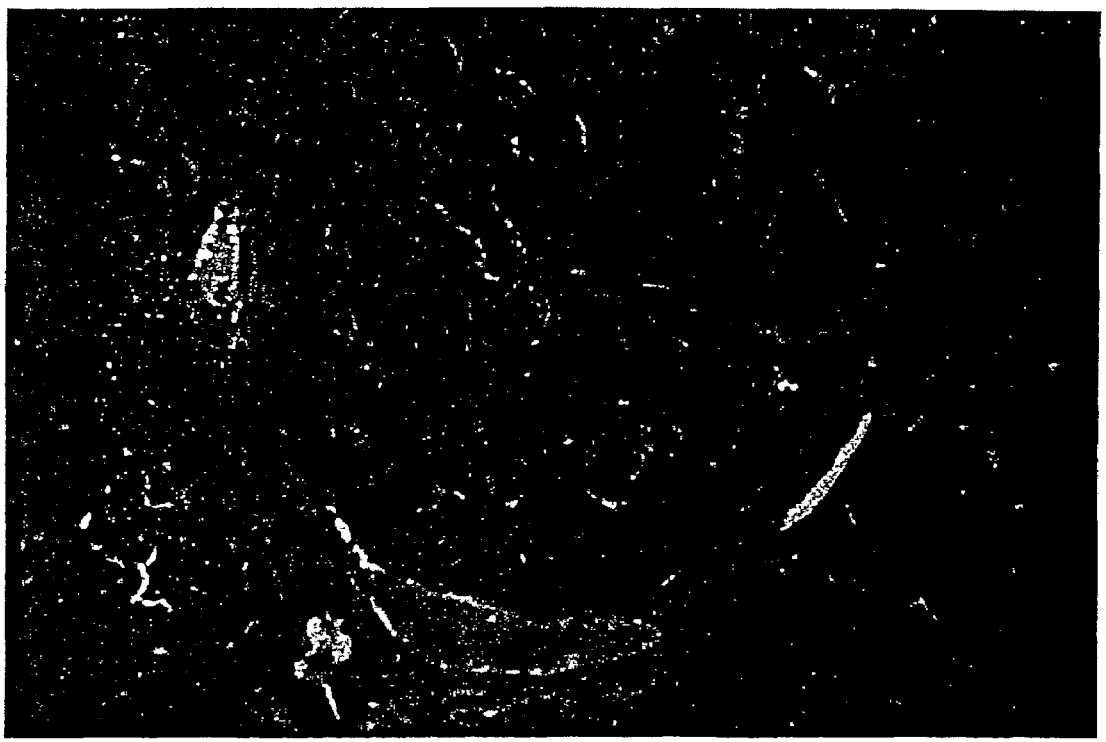
FIG. 6a is a photograph of liver tissue from the group to which DMN and oltipraz (5 mg/kg)/DDB (25 mg/kg) were co-administered (H&E staining).
Figure 6B:
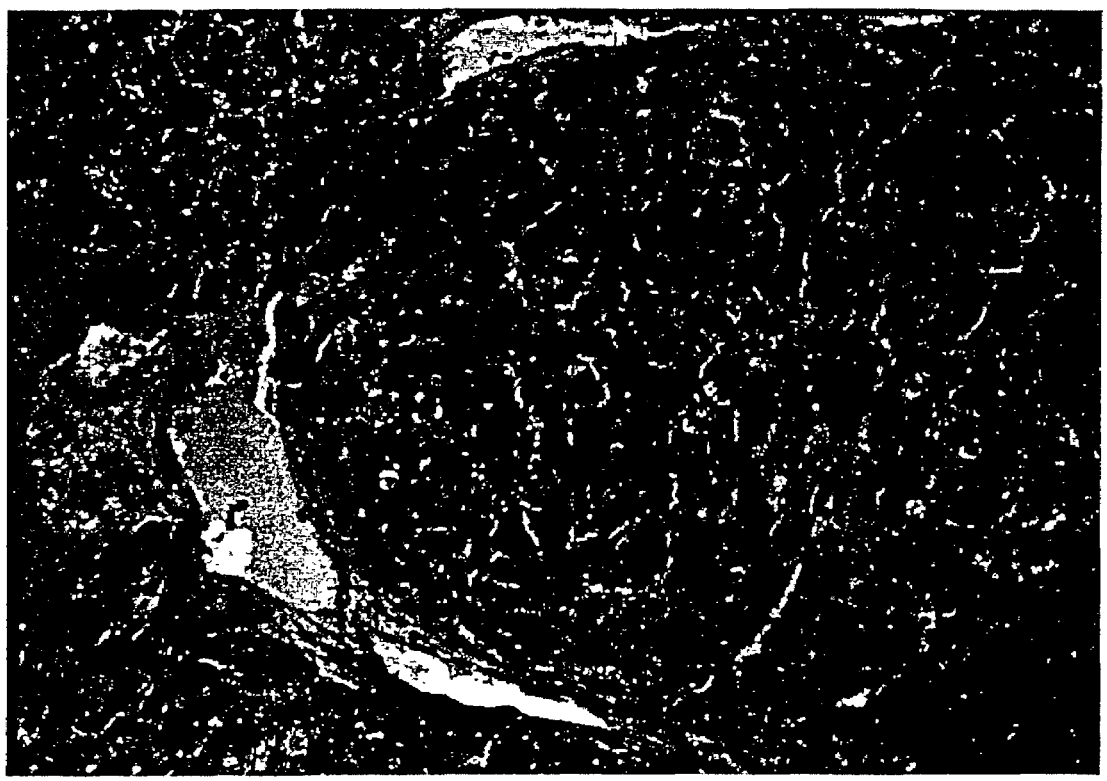
FIG. 6b is a photograph of liver tissue from the group to which DMN and oltipraz (5 mg/kg)/DDB (25 mg/kg) were co-administered (Masson's trichrome staining).

The tissue pathological effect of various oltipraz/DDB combinations on DMN induced hepatic fibrosis was observed in an animal test model. No hepatic fibrosis was observed in normal rats (FIGS. 2a and 2b). Clear fibrosis in the hepatic tissue was observed in rats one week after administering DMN over a 3-week period, 3 times a week (FIGS. 3a and 3b). When oltipraz and DDB were administered with a dosage ratio of 25:5 and 15:15 mg/kg over a 3-week period (3 times a week) one day after administration of DMN, fibrosis in the hepatic tissue was significantly reduced when compared to DMN administration alone. Especially, the animal group wherein oltipraz and DDB with a dosage ratio of 25:5 mg/kg were administered (FIGS. 4a and 4b) showed superior efficacy of the drug to that of the animal group in which oltipraz and DDB were administered with a dosage ratio of 15:15 mg/kg (FIGS. 5a and 5b) and 5:25 mg/kg (FIGS. 6a and 6b), and strongly inhibited the progress of hepatic fibrosis.

Hepatic tissue necrosis and fibrosis were pathologically determined through the use of pathological indicators for collagen accumulation, namely, Masson's trichrome staining. The degree of hepatic fibrosis was determined by evaluating the fibrosis value and Knodell score, which show degrees of liver damage and fibrosis.

TABLE 8

Inhibition Effect of Oltipraz/DDB Combination on Hepatic Tissue Fibrosis

| Group | Fibrosis Values | Knodell Values |
|---|---|---|
| Control | 0 | 0 |
| DMN | 2.9 ± 0.9 | 11.7 ± 1.8 |
| DMN + Oltipraz 25: DDB 5 mg/kg | 0.3 ± 0.5** | 2.0 ± 1.5** |
| DMN + Oltipraz 15: DDB 15 mg/kg | 0.3 ± 0.5** | 4.0 ± 1.2** |
| DMN + Oltipraz 5: DDB 25 mg/kg | 1.2 ± 0.6** | 6.0 ± 1.3** |

Each value is represented by the average ± standard deviation and the number of animals used was 8 to 10. The significance of each group is determined by the Newman-Keuls test of multiple analysis. The significance markers are: **=$p<0.01$ compared to DMN treated group. Degree of fibrosis was graded as 0=Normal, 1=Presence of weak fibrous tissue, 2=Moderate presence of fibrous tissue, 3=Obvious presence of fibrous tissue, 4=Evidence of severe fibrosis. Sum of values from periportal bridging (Greatest=10), intralobular cell loss (Greatest=4), portal inflammation (Greatest=4), and fibrosis (Greatest=4) yields the Knodell score.

Test Example 9

Effect of Oltipraz/DDB Combinations on TGF-β Expression

As addressed above, TGF-β is a cytokine that causes hepatic fibrosis and is known to be associated with hepatic fibrosis development. Table 9 shows changes in the presence of TGF-β mRNA by RT-PCR methods.

The DMN-administered group showed a significant increase in the production of TGF-β compared to the control group. In animals administered with altered oltipraz/DDB combination ratios, quantitative RT-PCR results regarding TGF-β expression show that administrations of 30 mg/kg of oltipraz and co-administrations of 25:5 mg/kg oltipraz and DDB completely inhibited TGF-β expression. However, as the DDB to oltipraz ratio increases, the inhibition of TGF-β expression is progressively lost. In the animal group administered with DDB alone, TGF-β expression was not inhibited. Therefore, inhibition of TGF-β expression is considered to be caused by oltipraz. On this ground, the best combination ratio of oltipraz to DDB is 5:1 (Table 9).

TABLE 9

Relative inhibition of TGF-β expression by oltipraz/DDB combination

| | DMN 10 μl/kg | DMN + oltipraz 30 mg/kg | DMN + DDB 30 mg/kg | DMN + oltipraz 25 + DDB 5 mg/kg | DMN + oltipraz 15 + DDB 15 mg/kg | DMN + oltipraz 5 + DDB 25 mg/kg |
|---|---|---|---|---|---|---|
| % Inhibition of TGF-β mRNA expression | 0 | 65 | 0 | 65 | 30 | 0 |

WORKING EXAMPLES

<Working Example 1>

| | |
|---|---|
| Oltipraz | 25 mg |
| DDB | 1 mg |
| Lactose | 50 mg |
| Starch | 10 mg |
| Magnesium stearate | Proper amount |

The above components are mixed and a tablet is prepared by a conventional tablet preparation process.

<Working Example 2>

| | |
|---|---|
| Oltipraz | 50 mg |
| DDB | 1 mg |
| Lactose | 50 mg |
| Starch | 10 mg |
| Magnesium stearate | Proper amount |

The above components are mixed and a tablet is prepared by a conventional tablet preparation process.

<Working Example 3>

| | |
|---|---|
| Oltipraz | 5 mg |
| DDB | 10 mg |
| Lactose | 50 mg |
| Starch | 10 mg |
| Magnesium stearate | Proper amount |

The above components are mixed and a tablet is prepared by a conventional tablet preparation process.

<Working Example 4>

| | |
|---|---|
| Oltipraz | 25 mg |
| DDB | 5 mg |
| Lactose | 30 mg |
| Starch | 28 mg |
| Talc | 2 mg |
| Magnesium stearate | Proper amount |

The above components are mixed and a capsule preparation is prepared by filling a hard gelatin capsule with the mixture through a conventional capsule preparation process.

<Working Example 5>

| | |
|---|---|
| Oltipraz | 25 mg |
| DDB | 5 mg |
| Lactose | 30 mg |
| Starch | 28 mg |
| Talc | 2 mg |
| Magnesium stearate | Proper amount |

The above components are mixed and a capsule preparation is prepared by filling a hard gelatin capsule with the mixture through a conventional capsule preparation process.

<Working Example 6>

| | |
|---|---|
| Oltipraz | 1 mg |
| DDB | 50 mg |
| Lactose | 30 mg |
| Starch | 28 mg |
| Talc | 2 mg |
| Magnesium stearate | Proper amount |

The above components are mixed and a capsule preparation is prepared by filling a hard gelatin capsule with the mixture through a conventional capsule preparation process.

<Working Example 7>

| | |
|---|---|
| Oltipraz | 5 mg |
| DDB | 25 mg |
| Lactose | 30 mg |
| Starch | 28 mg |
| Talc | 2 mg |
| Magnesium stearate | Proper amount |

The above components are mixed and a capsule preparation is prepared by filling a hard gelatin capsule with the mixture through a conventional capsule preparation process.

<Working Example 8>

| | |
|---|---|
| Oltipraz | 250 mg |
| DDB | 50 mg |
| Isomerized sugar | 10 g |
| Sugar | 30 mg |
| Sodium CMC | 100 mg |
| Lemon Flavor | Proper amount |
| (add purified water to total volume of 100 ml) | |

A suspension is prepared with the above components according to conventional suspension production methods. A 100 ml brown bottle is filled with the suspension and sterilized.

<Working Example 9>

| | |
|---|---|
| Oltipraz | 50 mg |
| DDB | 250 mg |
| Isomerized sugar | 20 g |
| Sugar | 20 g |
| Sodium alginate | 100 mg |
| Orange Flavor | Proper amount |
| (add purified water to total volume of 100 ml) | |

A suspension is prepared with the above components according to conventional suspension production methods. A 100 ml brown bottle is filled with the suspension and sterilized.

<Working Example 10>

| | |
|---|---|
| Oltipraz | 25 mg |
| DDB | 5 mg |
| Lactose | 30 mg |
| Starch | 20 mg |
| Magnesium stearate | Proper amount |

The above components are mixed and filled in a polyethylene coated envelope and sealed to prepare a powder.

<Working Example 11>

| 1 Soft capsule containing | |
|---|---|
| Oltipraz | 25 mg |
| DDB | 5 mg |
| Polyethylene glycol 400 | 400 mg |
| Concentrated glycerine | 55 mg |
| Purified water | 35 mg |

Polyethylene glycol is mixed with concentrated glycerin, and then purified water is added. Maintaining the mixture at 60° C., oltipraz is added to the mixture. The mixture is stirred at approximately 1,500 rpm. After the mixture has combined uniformly, the mixture is cooled at room temperature while slowly stirring. Air bubbles are removed with a vacuum pump, leaving the contents of the soft capsule.

The soft capsule membrane is manufactured according to conventional preparation methods using a widely known soft gelatin-plasticizer formula containing gelatin 132 mg, concentrated glycerin 52 mg, 70% disorbitol solution 6 mg per capsule, a proper amount of ethyl vanillin flavoring agent, and carnauba wax as the coating agent.

INDUSTRIAL APPLICABILITY

Oltipraz/DDB formulations according to the present invention exhibit surprisingly good effect on the treatment and prevention of liver fibrosis and cirrhosis. Thus, it may be clinically used for the treatment and prevention of liver fibrosis and cirrhosis.

What is claimed is:

1. A pharmaceutical composition for treating the progression of hepatic fibrosis and cirrhosis, comprising:
   5-(2-pyrazinyl)-4-methyl-1,2-dithiol-3-thione (oltipraz) and dimethyl-4,4'-dimethoxy-5,6,5',6'-dimethylene dioxybiphenyl-2,2'-dicarboxylate (DDB) in a weight ratio of 1:5 to 5:1.

2. The pharmaceutical composition according to claim 1, wherein the composition is formulated as a form selected from a group consisting of a capsule, a tablet, a soft capsule, a suspension, a syrup, an injection, and a powder.

3. The pharmaceutical composition according to claim 1, wherein the composition is for oral administration.

4. The pharmaceutical composition according to claim 1, wherein the composition comprises oltipraz and DDB in an oltipraz:DDB weight ratio of 5:1, 1:1 or 1:5.

5. A method for treating the progression of hepatic fibrosis and cirrhosis, comprising:

administering an effective amount of a pharmaceutical composition comprising 5-(2-pyrazinyl)-4-methyl-1,2-dithiol-3-thione (oltipraz) and dimethyl-4,4'-dimethoxy-5,6,5',6'-dimethylene dioxybiphenyl-2,2'-dicarboxylate (DDB) in a weight ratio of 1:5 to 5:1 to a mammal.

6. The method for treating the progression of hepatic fibrosis and cirrhosis according to claim 5, wherein the composition is formulated as a form selected from a group consisting of a capsule, a tablet, a soft capsule, a suspension, a syrup, an injection, and a powder.

7. The method for treating the progression of hepatic fibrosis and cirrhosis according to claim 6, wherein the composition is for oral administration.

8. The method according to claim 5, wherein the effective amount of oltipraz administered consists of 5 to 25 mg/kg mammal and the effective amount of DDB administered consists of 5 to 25 mg/kg mammal.

9. The pharmaceutical composition according to claim 1, wherein the composition comprises the oltipraz and the DDB in a weight ratio of 5:1.

10. The pharmaceutical composition according to claim 1, wherein the pharmaceutical composition treats the progress of dimethylnitrosamine-induced hepatic fibrosis and cirrhosis.

11. The method of claim 5, wherein the composition comprises the oltipraz and the DDB in a weight ratio of 5:1.

12. The method of claim 5, wherein the effective amount of the pharmaceutical composition per kg of the mammal comprises 25 mg oltipraz and 5 mg DDB; 15 mg oltipraz and 15 mg DDB or 5 mg oltipraz and 25 mg DDB.

13. The method of claim 5, wherein the method treats the progress of dimethylnitrosamine-induced hepatic fibrosis and cirrhosis.

14. The method of claim 12, wherein the effective amount of the pharmaceutical composition per kg of the mammal comprises 25 mg oltipraz and 5 mg DDB.

* * * * *